United States Patent [19]

Weeks

[11] Plant 4,047

[45] May 3, 1977

[54] ROSE PLANT

[76] Inventor: O. L. Weeks, 926 W. Philadelphia, Ontario, Calif. 91761

[21] Appl. No.: 693,737

[22] Filed: June 7, 1976

[51] Int. Cl.[2] ..... A01H 5/00

[52] U.S. Cl. ..... Plt./24

[58] Field of Search ..... Plt./24

*Primary Examiner*—Robert E. Bagwill

*Attorney, Agent, or Firm*—Frank B. Robb

EXEMPLARY CLAIM

1. A new and distinct variety of Rose plant of the Floribunda class, substantially as herein shown and described, characterized particularly as to novelty by the well formed buds which come in large measure on single stems, the buds retaining the Floribunda characteristics of clustering adequately to provide color mass, the excellent petal substance which provides long life to the flower, both on the plant and when cut, the vivid yellow coloring which holds well throughout the life of the flowers, and the well contained growth and upright development with little spreading effect.

1 Drawing Figure

The present invention relates to a new and distinct variety of rose plant of the Floribunda class, which was originated by me by crossing the rose variety known as "Arlene Francis" (U.S. Plant Pat. No. 1,684) with an unnamed and unpatented seedling which I have developed and which is designated in my records as No. 604-17, the former being the seed parent, and the latter being the pollen parent.

As the result of this breeding, I have produced a new and improved rose variety which is distinguished from its parents, as well as from all other rose varieties of which I am aware as evidenced by the following unique combination of characteristics which are outstanding in the new variety:

1. The well formed buds which come in large measure on single stems;
2. The fact that the buds retain the Floribunda characteristics of clustering adequately to provide color mass;
3. The excellent petal substance which provides long life to the flower, both on the plant and when cut;
4. Its vivid yellow coloring which holds well throughout the life of the flowers; and
5. Its well contained growth and upright development with little spreading effect.

In comparison with its pollen parent "Arlene Francis" which is a hybrid tea rose, having typical medium to large flowers and buds with classic, tight pointed, high centers, with smooth petal edges, my new variety is definitely a Floribunda, having a bud which is much more open with slight ruffling of the petal edges. Furthermore, there is substantially more petal substance in my new variety than in the seed parent, and the foliage is more leathery and glossy.

My new variety may show some weathering, depending upon the season, there being a slight reddish tipping of the petals at such time, whereas the seed parent remains at all times the smooth yellow with no such changes.

Referring to the seed parent, the seedling which I designate 604-17, it is noted that this seedling was a short growing plant, nearly like a miniature Hybrid Tea Rose. The pollen parent flowers were medium to small in size, and came always on single stems with near perfect classic petal conformation and of extremely stiff petal substance so as to appear almost artificial. The buds and flowers of my new variety are much more informal with slightly open centers of the bud and typical clustering, more in the nature of a Floribunda. The pollen parent color was a smooth, light yellow, whereas the new variety is a deeper yellow color, having the characteristic of producing reddish edging at certain times of the year. While the pollen parent flowers were borne with completely smooth petal edges, the new variety has flowers with slightly serrated edges.

Asexual reproduction of my new variety by budding made at Ontario, Calif., shows that the aforementioned characteristics and distinctions come true to form, and are established and transmitted through succeeding propagations.

The accompanying drawing shows typical specimens of the vegetative growth and flowers of my new variety, and as depicted in color as nearly true as is reasonably possible to make the same in a color illustration of this character.

The following is a detailed description of my new variety, with color terminology in accordance with Munsell's Color Cascade, published by Munsell Color Company, Inc., of Baltimore, Md., except where general color terms of usual dictionary significance are accurately definitive:

Type: Hardy; bush; outdoor; seedling; for cut flowers and for garden decoration.

Class: Hybrid floribunda.

Breeding: Seedling (No. 6951).

*Seed parent.*—"Arlene Francis" (U.S. Plant Pat. No. 1,684).

*Pollen parent.*—An unnamed seedling (my designation No. 604-17).

Propagation: Holds its distinguishing characteristics through succeeding propagations by budding.

FLOWERS

Locality where grown and observed: Ontario, Calif.

Flowers borne: Several to a stem in regular, pyramidal clusters on normally strong medium to long length stems.

Quantity of bloom: Free and abundant, outdoors and in the greenhouse.
Continuity: Continuous.
Fragrance: Slight.
Bud:
*Peduncle.*—Medium to long; medium to heavy caliper; erect; medium smooth. Color — Yellowish green; with few reddish brown hairs.
*Before calyx breaks.*—Size — Medium to small. Form — Medium length, globular with a conspicuous neck; with foliaceous appendages on the surface of the bud; with slender, bristle-like foliaceous parts extending beyond the tip of the bud to ½ or more of its length. Color — Light yellowish green.
*As calyx breaks.*—Color — Not significant.
*As petal first opens.*—Size — Small. Form — Long and flat. Color — Outside — Yellow 27-3; Inside — Yellow 27-5.
*Opening.*—Opens up well.
Bloom:
*Size (when fully open).*—Medium; from 2½ inches to 3 inches in diameter.
*Petalage.*—Double (more petals, but stamens not hidden); from 20 to 25 petals.
*Form.*—Full, high-centered at first, becoming very open although still somewhat high-centered; petals being at first tightly cupped, slightly rolled outward; becoming later at maturity loosely rolled outward and downward.
Petals:
*Texture.*—Moderately thick; soft; with velvety inside; with velvety outside.
*Shape.*—Outside — Obovate; with apex rounded. Intermediate — Obovate with slightly rounded apex. Inside — Obovate; scalloped slightly with apex slightly rounded.

This description was made from a rose grown outdoors in the month of September at Chino, Calif.:

*Color.*—Outer petal — Outside surface — Yellow 26-4 blending quickly to 26-3 then back to 26-5 then the upper half of the petal to 26-3. Inside surface — Yellow 27-5 blending ½ way up to 26-3.
*Intermediate petal.*—Outside surface — Yellow 27-4 slightly changing to 26-3 switching to top half of petal 27-4. Inside surface — Yellow 27-5 blending ½ way up to 27-4.
*Inner petal.*—Outside surface — 27-5. Inside surface — Yellow 27-6 with streaks of 39-5 Pink.

This description was made from a rose that was open for three days indoors in the month of September at Chino, Calif.:

*Color.*—Outer petal — Outside surface — Yellow 26-4 encircled at the base by 27-5 with 26-4 continuing up to the top with the apex 26-3. Inside surface — Yellow 27-5 changing ½ way up to 27-4.
*Inside petal.*—Outside surface — 27-4 Yellow. Inside surface — Yellow 27-5 changing ½ way up to 27-4.
*General color effect.*—Newly opened flower — Center of flower somewhat darker 27-4 than the outside of bloom 26-4. 3-days open — Basic yellow 27-5 without color change.
*Flower longevity.*—On bush in garden — 4 to 5 days in September. At living room temperatures — 5 to 6 days.

REPRODUCTIVE ORGANS

Stamens: Many; arranged regularly about pistils, tucked in calyx.
Filaments: Medium length.
*Color.*—Yellow; many with anthers.
Anthers: Medium to large; all open at once.
*Color.*—Dark yellow.
Pollen: Sparse.
*Color.*—Gold yellow.
Pistils: Many.
Styles: Long length; medium caliper; bunched and columnar.
Stigma:
*Color.*—White.
Ovaries: All enclosed in calyx.
Hips: None observed.
Sepals: Permanent; short to medium long; spear-shaped; recurved.
*Color.*—Light green.

PLANT

Foliage:
*Leaves.*—Compound of 5 leaflets; normally abundant; medium size; soft, leathery; semi-glossy.
*Leaflets.*—Shape — Obovate. Apex — Acute. Base — Acute. Margin — Irregularly serrate.
*Color.*—Mature — Upper surface — Normal green. Under surface — Light yellowish green. Young — Upper surface — Moderately light, yellowish green. Under surface — Moderately light, yellowish green.
*Rachis (the supporting stem of the compound leaf).*—Light weight. Upper side — Smooth mostly, slightly grooved. Under side — Moderately smooth.
*Stipules.*—Medium long; medium width; points of average length turning out at an angle of less than 45°.
*Disease resistance.*—No evidence of blackspot and good resistance to powdery mildew and rust; also good resistance to rose insects.
Growth:
*Habit.*—Well proportioned; bushy; much branched.
*Growth.*—Vigorous.
*Canes.*—Moderately heavy caliper.
*Main stems.*—Color — Light green. Large prickles — Many; long; straight, slightly downward with narrow base. Color — Light dusty brown. Small prickles — Few. Color — Light brown. Hairs — None. Branches — Color — Dull yellowish green. Large prickles — Few; medium to long; straight, hooked slightly downward; long, narrow base. Color — Dark Brown. Small prickles — Few. Color — Dark Brown. Hairs — None.
*New shoots.*—Color — Dull green with maroon tint. Large prickles — Few; medium to long; hooked downward; with long narrow base. Color — Red. Small prickles — None. Hairs — None.

I claim:

1. A new and distinct variety of Rose plant of the Floribunda class, substantially as herein shown and described, characterized particularly as to novelty by the well formed buds which come in large measure on single stems, the buds retaining the Floribunda characteristics of clustering adequately to provide color mass, the excellent petal substance which provides long life to the flower, both on the plant and when cut, the vivid yellow coloring which holds well throughout the life of the flowers, and the well contained growth and upright development with little spreading effect.

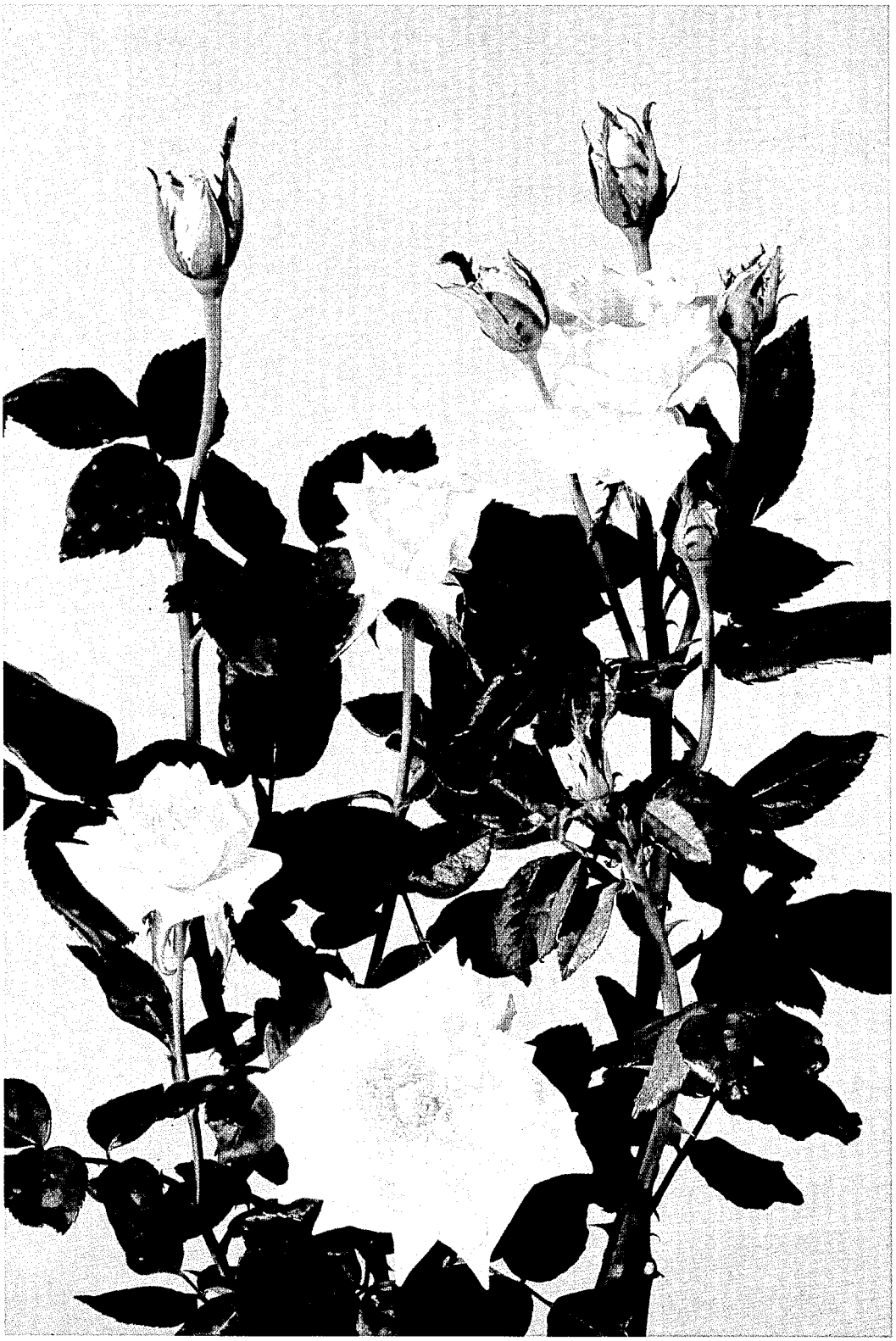

* * * * *